United States Patent [19]

Tanne

[11] Patent Number: 4,691,716

[45] Date of Patent: Sep. 8, 1987

[54] AUTOMATIC CORNEAL SURGERY SYSTEM

[76] Inventor: Emanuel Tanne, 6517 Buena Vista Dr., Vancouver, Wash. 98661

[21] Appl. No.: 867,039

[22] Filed: May 27, 1986

Related U.S. Application Data

[62] Division of Ser. No. 814,223, Dec. 27, 1985, Pat. No. 4,665,914.

[51] Int. Cl.$^4$ ............................................... A61B 5/10
[52] U.S. Cl. ...................................... 128/774; 33/551
[58] Field of Search ..................... 128/774, 305, 305.1; 364/560; 351/212; 33/512, 507, 175, 551, 552

[56] References Cited

U.S. PATENT DOCUMENTS 3,781,096 12/1973 Townsley ............................ 351/212
4,593,473 6/1986 Shimomura ....................... 33/551 X

OTHER PUBLICATIONS

Kam et al, Journal of Bioengineering, vol. 2, pp. 21–26, 1978.
Ayres et al; Electrical Touch Probe, Conference Proceedings, 4/1980.
Armstrong et al, Method for Measuring Shapes; Biomechanics, vol. 12, No. 5, 1979.

*Primary Examiner*—W. E. Wayner
*Attorney, Agent, or Firm*—Chernoff, Vilhauer, McClung & Stenzel

[57] ABSTRACT

An instrument for automating corneal surgical procedures, such as radial keratotomy and other corneal operations, which includes one or more probe sensors with extendible tips which, by measuring electrical resistivity, are responsive to contact occurring with the corneal surface. Positioning of the probe sensor(s) over various points of the corneal surface provides data signals which enable the surface topography of the cornea to be mapped by a micro-processor. A surgical knife having automatic depth control is provided whose operation is regulated in response to changes in the electrical resistivity between the knife and the human body as penetration is made into the layers of the cornea. The probe sensor(s) and knife are used with a ring-like fixture attachable by vacuum to the eye and comprised of a fixed outer ring and a movable inner ring, the fixture providing mounting and/or support for these elements while permitting their movement to different meridial locations by rotation of the inner ring. One arch element bridging a diameter of the ring fixture supports the probe sensor(s) and a second arch element has guideways thereon for controlling the movement and positioning of the knife. In a modification, small motors, controlled by the micro-processor, drive the probe sensor(s) and knife in their respective movement over the corneal surface.

9 Claims, 8 Drawing Figures

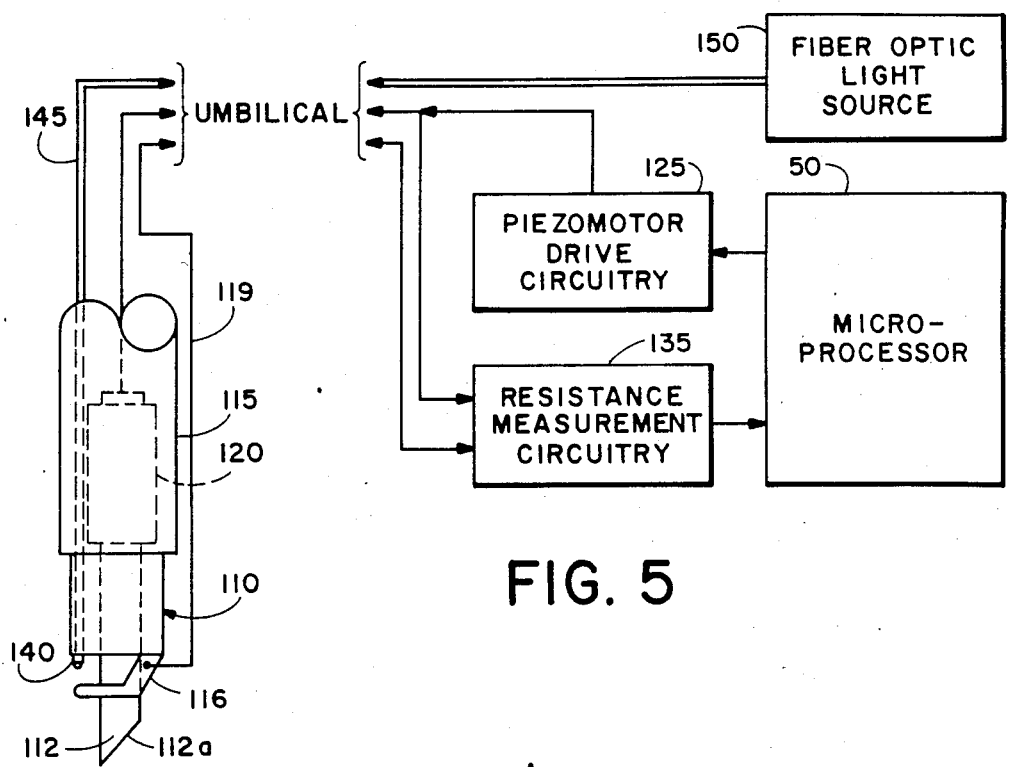
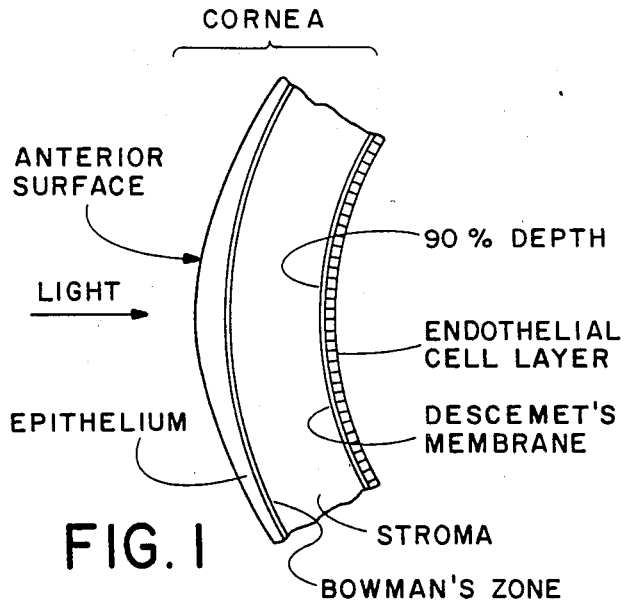
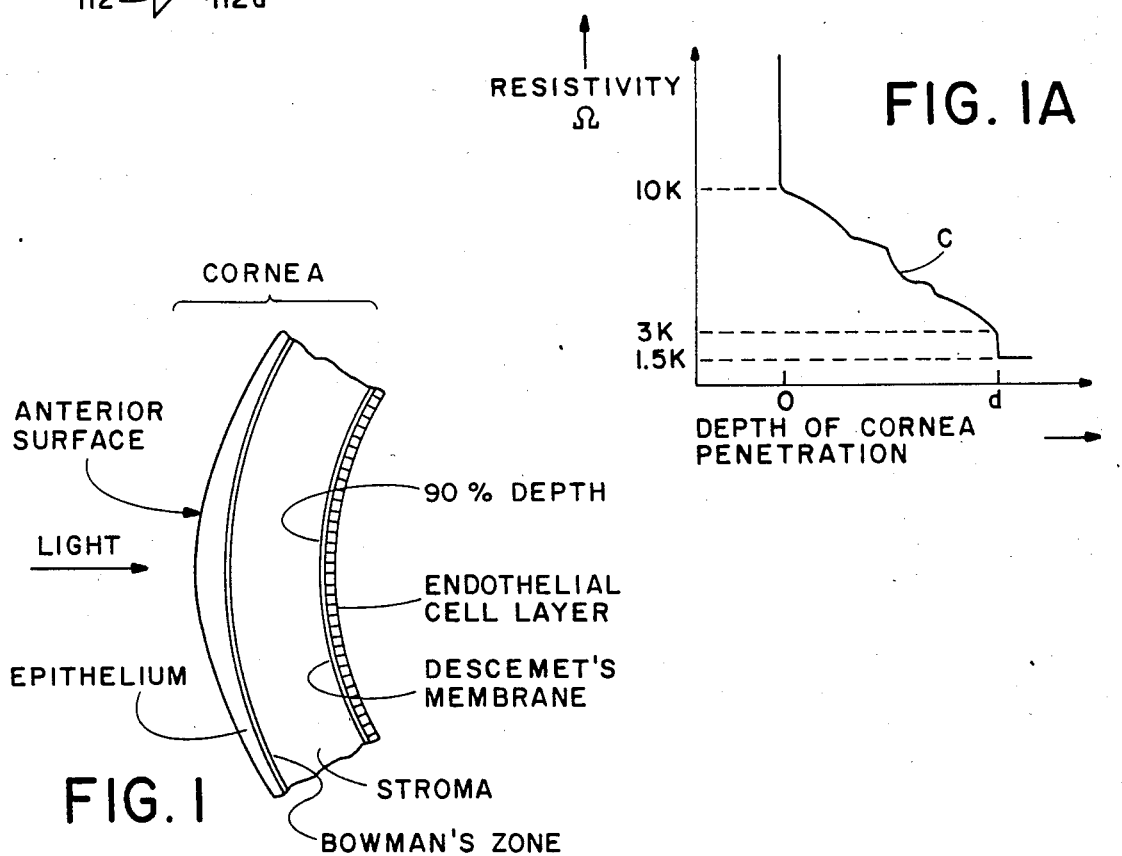

AUTOMATIC CORNEAL SURGERY SYSTEM

This application is a division of application Ser. No. 814,223, filed Dec. 27, 1985 now U.S. Pat. No. 4,665,914.

BACKGROUND OF THE INVENTION

The present invention is directed to a system for automating corneal surgical procedures such as radial keratotomy, for example, and, more particularly, to means for accurately mapping the topography or surface configuration of the cornea and for automating and controlling the depth of cut made into the corneal tissue by the surgical knife.

Radial keratotomy, as well as other corneal surgical procedures, have experienced increased interest in an attempt to surgically correct refractive errors and thereby, if possible, remove the need for eyeglass correction. Radial keratotomy, originated by Fyodorov of the Soviet Union, is one of many new surgical techniques, along with keratomileusis, epikeratophakia and others, which have evolved in the past 25 to 30 years. Radial keratotomy achieves its results by flattening the cornea with radial incisions which begin paracentral to the corneal center, leaving an untouched central corneal zone of 3-4 mm in diameter, and extend peripherally. In the procedure currently practiced, 8 to 16 cuts are made into the thickness of the cornea. The primary function in creating these radial incisions on the external surface of the cornea is to reduce myopia (near-sightedness). At the present time it is estimated 100,000 patients have undergone the radial keratotomy operation in the United States.

While the complication rate is low and the operation relatively safe, the predictability of end results had been the major stumbling block. The operation is presently done on myopic patients ranging from 2 to 6 diopters of myopia. The results vary significantly from surgeon to surgeon although the same number of cuts from the edge of the same size optical zone may be done by each. A particularly important finding in many of the studies on the results of radial keratotomy has been the influence of the depth of incision on the degree of final refractive correction. Those procedures which had a relatively shallow cut produced the least amount of correction and the amount of ultimate regression of this effect was greatest in these patients. It has been learned that cutting approximately 90% of the thickness of the cornea throughout the entire length of the incision will produce the most flattening of the cornea and the most gain in the reduction of myopia. It should be here noted that the peripheral cornea is thicker than the paracentral and central corneal zones. This means that in order for a surgeon to cut the entire length of the incision at 90% thickness, he must redeepen the peripheral cut and he does this by random judgment. Redeepening procedure has the risk of perforation of the cornea and entrance into the anterior chamber of the eye. This significantly increases the risk for potential infections and complications such as damage to the corneal endothelial cell layer and the formation of cataracts.

Additional problems include the fact that the actual thickness of the cornea cannot be adequately measured by any known pachometer with consistent results. All instruments presently used vary in the reporting of the corneal thickness. It is estimated that the central cornea is approximately 500 microns and the peripheral cornea may be as thick as 580 or 600 microns. Since the current level of accuracy of optical and electronic pachometer measurements leave much to be desired in terms of accuracy, it is therefore virtually impossible for a surgeon to be able to consistently cut freehand at 90% of corneal thickness. (It should also be noted that corneal thicknesses vary from patient to patient.) Also thickness changes occur the moment the cornea is incised with the initial incision because the cornea incision will swell. At present all cutting of the cornea is done freehand by the surgeon in the following manner. The surgeon takes a pachometer reading and then, based on the site of the thinnest corneal reading, he sets the depth of cut of the knife that is to be used which may be either a diamond or a metal blade knife. Many surgeons presently set their blades at 100% corneal thickness in order to create the deepest cut. It is apparent that the exact depth of cut is not known in such circumstances and, since there is no penetration, it is equally apparent that either the pachometer readings are incorrect or the surgeon's setting of the knife blade is inaccurate. The desired result of obtaining a 90% thickness in cut over the full length of the incision cannot be achieved by this technique. Only a technique which takes into consideration the variation in corneal thickness in an unoperated upon cornea, as well as during the actual cutting procedure, can produce a 90% cut.

Another important area that is not fully understood, but which is important in understanding the result in terms of predictability, is the change in the topography (or surface contour) of the cornea. Measurement of corneal topography is required to define the corneal curvature before and after an operation. The anterior corneal refracting surface is the major focusing element on the eye. This surface has a power of about 49 diopters of convergence, and the posterior corneal surface has about 6 diopters of divergence. This corneal combination contributes about 43 diopters of convergence to the eye focusing systems, and the lens of the eye contributes about another 20 diopters of convergence. For a $\pm 0.1$ diopter accuracy, and a $\pm 0.05$ diopter repeatability requirement, a corneal topography measuring system will need to measure the distance between a reference and the corneal surface to an accuracy within 20 microns.

At the present time there is no satisfactory method to fully delineate during surgery, but prior to the actual cutting and postoperatively after the cutting, the true corneal topography. Photographic methods both conventional and photo electronic keratometers which essentially photograph light rings placed on the cornea, are inaccurate. Many of these do not reach the entire length of the cornea. They also cannot be used once the corneal surface has been disrupted and reflectivity has been altered, and thus they cannot be used during surgery. Measurements taken preoperatively by all of these conventional instruments obtain an average curvature prior to surgery and, therefore, fail to define clearly the true extent of changes in corneal topography in the peripheral cornea. The photoelectric keratometers only approximate the actual curvature changes on the corneal surface and do not truly define the exact relationship of the changes in curvature of the corneal surface. Therefore, at the present time there is no device that can be used intra-operatively which will accurately measure the complete corneal topography both prior to and immediately after incisions. In order to produce consistent results, a consistent cut and true topography measurement are necessary. It is only with the obtaining of this information that will there be an opportunity to correlate the final refractive change that has been created in a patient. Other factors such as age, scleral rigidity and intraocular tension, while playing some role, can be factored into the final predicted end result.

BRIEF SUMMARY OF THE INVENTION

The corneal topography measuring means of the present invention utilizes a ranging technique responsive to the electrical resistivity exhibited by the corneal tissue to take simultaneous readings at a plurality of points along any meridian over the entire length of the corneal surface. These meridians can be selected by the operating surgeon at any time, either prior to the actual surgery as well as during and after the actual incisions have been made. These topography measurements, which provide at any given moment the true topography of the cornea, can then be used for any corneal procedure or cataract type operation. Another facet of the present invention is the provision of means, responsive to variations in the electrical resistivity of the layers of corneal tissue, for precisely controlling the depth of cut of the surgical knife in radial keratotomy and other eye surgery procedures.

The automatic surgical knife has the ability to seek a 90% depth, or any other depth desired by the surgeon. This occurs automatically and during the cutting procedure the surgeon does not alter the depth of incision of the cutting instrument by any of his/her movements. The blade moves automatically in a vertical fashion seeking the desired depth. Therefore, with the use of this particular knife all cuts will be exactly the same regardless of the degree of skill, steadiness of hand or other attributes of the surgeon performing the operation. This same instrument can also be used to cut with high precision a circular hole which would greatly facilitate and improve the results of corneal transplant operations. Inability to create a truly circular cut has led to high postoperative corneal transplant astigmatism and is the leading cause of optical failures in patients who have undergone otherwise successful corneal transplant surgery.

The innovative advantages and features of the automated corneal surgery system of the present invention include:

The utilization of the electrical resistance exhibited by the cornea and its layers as a mechanism for mapping the topography of the eye and for controlling the depth of penetration into the cornea of a surgical knife.

A new and improved method and means for performing radial keratotomy and other surgical procedures on the eye in highly automated, precise and safe fashion.

A new and improved instrument for mapping the surface configuration of the cornea.

A new and improved surgical knife for cutting into the corneal tissues of the eye to a preset and uniform depth.

A vacuum fixation ring means for supporting the corneal mapping instrument and surgical knife on the eye.

A guide means with stops thereon for guiding the direction and length of the cut into the cornea of the surgical knife.

The foregoing and other objectives, features and advantages of the invention will be more readily understood upon consideration of the following detailed description of the invention, taken in conjunction with the accompanying drawing.

BRIEF DESCRIPTION OF THE DRAWING

FIG. 1 is a cross-sectional diagrammatical view of the various tissue layers forming the cornea of the human eye.

FIG. 1A is a curve representing the change of electrical resistivity of the cornea as a function of the depth of penetration therein of a probe.

FIG. 5 is a partly mechanical and partly diagrammatical view of an illustrative embodiment of the surgical knife portion of the automated radial keratotomy system of the present invention.

DETAILED DESCRIPTION OF THE INVENTION

FIG. 1, a diagrammatic and labeled illustration of the corneal layers of the eye, will be helpful as background in understanding the anatomic and physiological phenomena utilized in the automated radial keratotomy system of the present invention as hereinafter described.

FIG. 1A is a curve, c, representative of the electrical resistivity of the cornea, in a dry condition, as a function of the depth of penetration therein of a needle probe. The curve is taken from a paper by J. Kam et al. entitled "Controlled Mechanized Trepan" appearing in the *Journal of Bioengineering*, vol. 2, pp. 21-26, 1978. The resistivity, initially at a very high value before contact is made, is approximately 10 K ohms at the point of contact, o, of the probe with the outer layer of the cornea. The resistivity decreases gradually and rather smoothly to about 3K ohms as the probe penetrates deeper, but then exhibits a sudden drop to about 1.5K ohms as the probe reaches the last tissue layer of the cornea, d, which is about 0.03 mm thick and corresponds approximately to about a 90-degree depth of penetration (The resistivity values indicated are approximate and were measured by Kam et al. in experiments on the eyes of dogs.)

Figure 2:
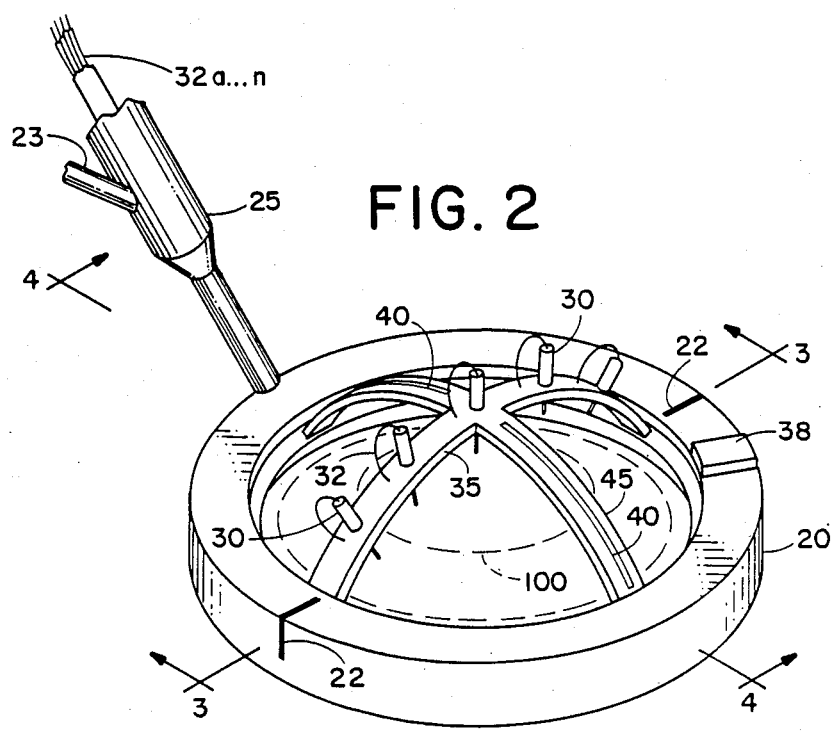
FIG. 2 is a pictorial view of a portion of an exemplary embodiment of the automated corneal surgery system of the present invention comprising in a single instrument a plurality of sensor probes for corneal topography mapping, a pair of guideways for the automated surgical knife and a mounting ring.
Figure 3:
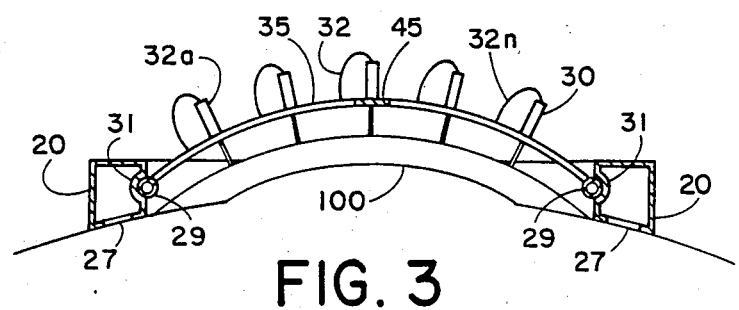
FIG. 3 is an elevational sectional view of the system embodiment taken in the plane of the sensor probes along the line 3—3 in FIG. 1.
Figure 4:
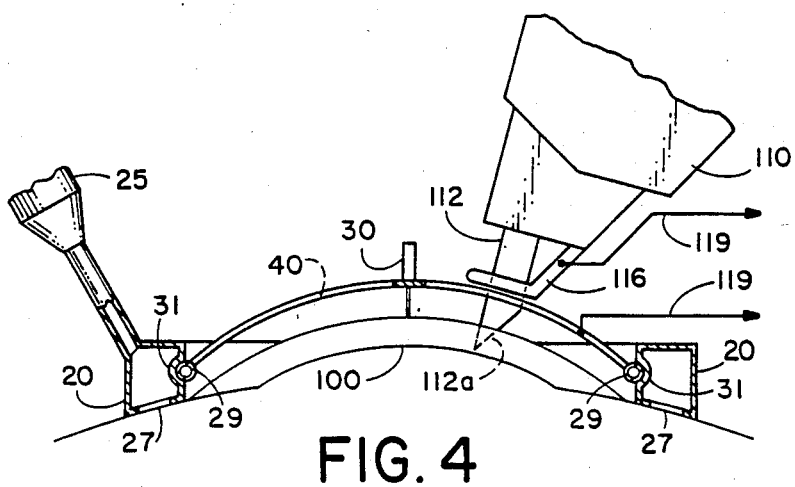
FIG. 4 is another elevational sectional view of the system embodiment of FIG. 1 taken in the plane of the knife guideways along the line 4—4 in FIG. 1, and also showing the operative portion of the knife.

Referring now to FIGS. 2-4, the system comprises a vacuum fixation ring and housing 20 for mounting onto the eye and supporting a plurality of probe sensors 30 with associated leads and knife guides 40 above the corneal surface thereof. Suction is applied by means (not shown) to the mounting ring via tube 23 feeding into hollow conduit 25, the resulting vacuum, applied to the eye's perimeter surface via a circular channel opening 27 on the underside of the housing 20, providing a secure mounting of the instrument to the eye while the operational procedures hereinafter described are performed. Extending as bridges over diametrical portions of the mounting ring are a pair of arch elements 35, 45 which carry the probe sensors and knife guideways, respectively. The arch elements are preferably offset from each other by 90 degrees although this spacing is not essential to the operation of the invention. Both arch elements connect at their tips to an inner ring 29 which rides in raceway channel 31 formed in the inside wall of the annular mounting ring housing 30. Electrical leads 32 to and from the individual probe sensors 30, not shown in all views for sake of clarity in the drawing, are brought as a bundled cable 32a . . . n into the hollow mounting ring housing 20 via the conduit 25 through which the vacuum suction is also supplied. Since the inner ring 29 is rotatably mounted relative to the fixed ring 20, the electrical leads 32a . . . n are coupled to their respective individual probe sensors via a suitable means, such as the provision of a plurality of slidable contacts, which enable the respective leads to couple electrically with their associated sensors as the inner ring is rotated into different orientations relative to the fixed ring housing. (Since the amount of relative rotation need not exceed 180 degrees to cover mapping of the full circular surface of the cornea 100, the necessary electrical connections could also be maintained to the sensors by coupling the individual leads 32a . . . n directly to their associated sensors via the arch element 35 with coiled extensible portions at the point where an end of the arch element meets the mounting ring 20 so as to provide the necessary play to permit half-circle rotation of the inner ring 29.)

Figure 6:
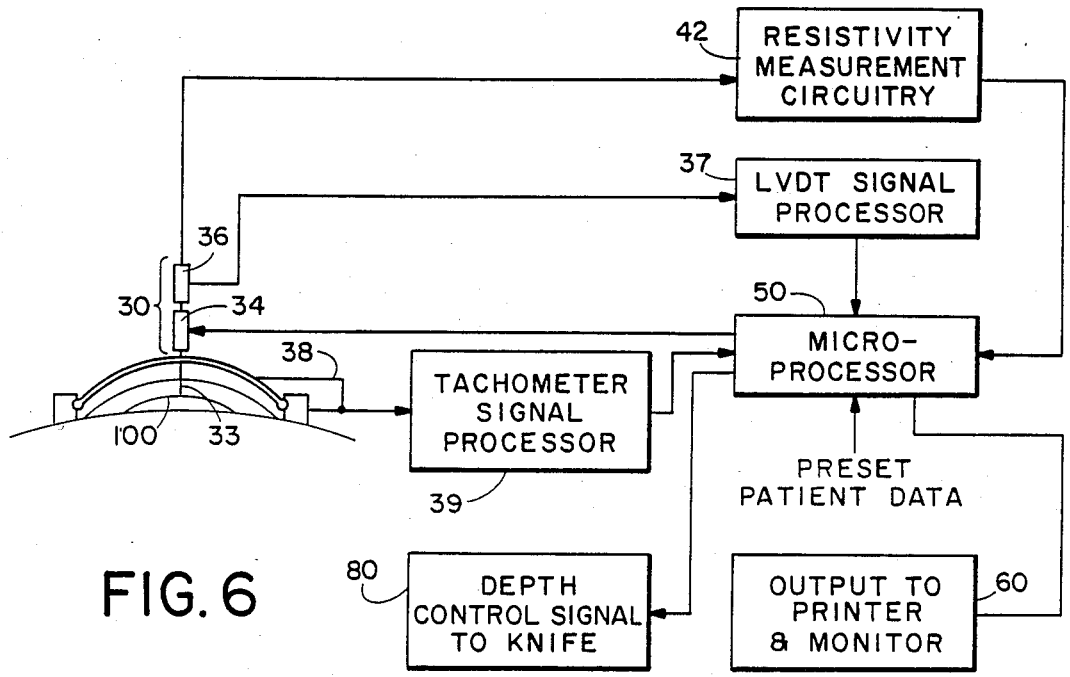
FIG. 6 is a partly schematic and partly diagrammatic view of the automated radial keratotomy system of the present invention.

Each of the probe sensors 30, as best illustrated in FIG. 6, comprises an extendible needlelike conductive tip 33 whose length of projection is controllable by a linear piezo-motor element 34. A linear velocity differential transformer (LVDT) 36 precisely monitors the displacement of the probe tip to a resolution of one micron, as it is extended (and retracted) by electrical actuation of the piezo-motor element 34, and generates an electrical analog signal which is representative of the position of the end of the needle tip. This information signal, after processing by circuitry 37 comprising, for example, an amplifier, filter and integrator coupling to an analog-to-digital converter, is in turn supplied as a digital signal to a micro-processor 50 which computes the instantaneous location of the needle tip relative to a reference location, and performs the same calculation for each of the plurality of individual probe sensors 30a . . . n spaced along the length of the arch element. As the inner ring 29 is rotated to different orientations relative to the fixed outer ring, the degree of radial displacement, relative to a reference location, is monitored by a digital tachometer element 38 and its signal, after processing by decoding circuitry 39, also supplied to the micro-processor 50. (To accomplish this monitoring function a plurality of magnetized spots could, for example, be spaced around the periphery of the inner ring 29 and a pair of magnetic sensing heads provided in the tachometer housing 38 to both count incremental radial changes and determine the direction of rotation.) Thus, the micro-processor receives a plurality of data signals, from each of the probe sensors, as rotation of the inner ring occurs, which, through suitable processing by means and techniques well known to the art, generates points of data representative of the location of the tip ends of the respective needle probe sensors at each of a plurality of meridian measurement locations extending over the circular corneal surface.

As an adjunct or alternative to the use of a digital tachometer to track the radial displacement of the inner ring the operating surgeon, with the aid of an angularly graduated circular reticle on the eyepiece of his/her operating microscope, and a marking device such as a pen containing methylene blue, could place meridial reference spots 22 on the perimeter of the patient's eye, coinciding with corresponding markings on the outer ring 20 of the instrument. This would enable the surgeon to remove and replace the instrument over the eye as desired while maintaining the same reference setup. With the operating microscope lined up over the instrument the spaced angular gradiations on the reticle would enable the surgeon to rotate the inner ring 29 to the desired radial increments to match the data point locations called for by the micro-processor 50 in performing the cornea mapping program over the surface of the cornea. For example, the inner ring 29 could be rotated in 30-degree increments, with data measurements taken by the probe sensors 30 at each location, to generate six meridial sets of data points.

As explained earlier, it has been discovered that the resistivity of the cornea at contact with the anterior surface is about 10 K ohms. Thus, as each needle is incrementally extended by the actuation of its associated piezo-motor 34, the resistance of the needle tip 33 to ground, as measured by a resistivity monitor 42 comprised, for example, of a constant current AC source with a voltage monitoring circuit coupled to each of the respective needle tips, either by hardwiring or by a time-sharing sequential strobing circuit, is at a very high value before contact is made with the corneal surface immediately below, and then drops to about 10K ohms at the point of contact with the tear surface. Consequently, monitoring of the depth of extension of each probe sensor needle tip, provided by its respective LVDT 36 and associated electronics 31, enables the determination of points on the corneal surface relative to a fixed reference location provided by the instrument mounted onto the eye. Rotation of the inner ring 29 to different meridian locations then enables another set of corneal surface locations points to be measured, and so on. In such fashion, by taking a plurality (exemplarily six) of meridial measurements at spaced radial locations (exemplarily at 30-degree spacing) a sufficient number of data points representative of the corneal surface locations can be obtained to generate, through computer processing in the microprocessor 50, a highly accurate map representation in computer memory of the topography or surface configuration of the cornea under measurement. This topographic representation can then be further processed and provided as an output 60 to a display device such as a printer and/or video monitor. In addition, the microprocessor, in conjunction with data preselected for each individual patient regarding the deepness of corneal cut to be made, inputed by the surgeon/operator, can provide another output signal 80 for regulating the depth of cut of a surgical knife in performing, for example, a radial keratotomy procedure, as will hereinafter be further described.

In FIG. 5 an exemplary embodiment of a surgical knife 110 is shown comprised of a hollow knife holder/-housing 115, a cutting blade 112, metallic guard element 114 attached to the end of the housing and projecting in front thereof, and an illumination lamp 140 provided by a fiber optic bundle 145 connected to a light source 150. A piezo-motor 120 is also provided inside the knife housing for incrementally and precisely extending and retracting the blade in response to signals provided by the drive circuit 125 which in turn receives controlling signals from the micro-processor 50. The radial orientation of the knife blade 112 relative to the axis of the knife housing 115 is manually adjustable so that the surgeon can select any desired orientation of the blade tip and lock it into that position for a particular procedure. Resistance measurement circuitry 135 is provided for monitoring and measuring the resistance existing between the knife and a probe sensor 32 in contact with the corneal surface and for determining when electrical contact exists between the guard element 116 and the guide element on the arch 45, and these measurement and monitoring signals are supplied to the micro-processor.

As the blade of the knife cuts deeper into the corneal tissue 100, the resistance in the electrical path between the blade tip and the needle probe on the corneal surface also drops in the manner earlier described. As the blade reaches the last tissue layer of the cornea, Descemet's membrane, corresponding to about a 90-percent depth of cut (see FIG. 1A), the resistivity decreases abruptly from about 3K ohms to about 1.5K ohms. By setting the instrument for a threshold sensitivity of about 2K ohms, an appropriate control signal can be outputed from the micro-processor when the desired 90-percent depth of cut level is achieved so as to stop the further extension of the knife blade 112.

Referring back to FIG. 4, the knife 110, used in association with the corneal surface contour mapping instrument and under the control of the same micro-processor 50, can perform, in highly automated fashion, a radial keratotomy procedure. The partially-retracted blade is inserted into one of the pair of slitted guides 40 formed on the meridial arch element 45, with the knife's guard element 116 abutting against the upper surface of the guide to provide a rest position for the knife. Upon the guard's contacting the guide an electrical path is closed which then provides an enable signal via leads to permit operation of the drive circuitry actuating the kinfe. When this contact is broken, by the lifting of the knife off the guide, the knife drive circuitry is disabled. It will be seen that, while the knife can not be brought any closer to the eye because of the shielding action provided by the guard 116 resting on the surface of the arch 45, the knife can be freely drawn along an approximately demimeridial length of the corneal, subject to the natural stops provided by the respective ends of the guide slit 40. Thus, while the surgeon has manual control of the knife's position along the particular corneal meridian over which the knife is positioned, the knife blade cannot be manually moved any closer to the eye, this latter movement being controlled exclusively (subject to user input and override) by the automated operation of the instrument of the present invention.

In carrying out a radial keratotomy procedure the knife blade is first brought to a point near or at one of the ends of the guideway 40. Then, assuming the instrument is set for a 90-percent depth of cut, the knife blade 112 is extended by controlled actuation of its piezo-motor until first, contact is made with the corneal surface, and then on until the marked drop of resistivity occurs which signals that the last tissue layer of the cornea, corresponding to the desired depth of cut, has been reached, at which point the further extension of the blade is automatically halted. The surgeon then draws the knife within the guideway along the meridian, with the blade being continuously incrementally extended and retracted, as required, to maintain a uniform 90-percent depth of incision into the cornea. (Obviously, the speed response of the system in monitoring and controlling blade depth must be sufficiently fast to safely keep up with the speed of the surgeon's incision.) Each of the foregoing steps is then repeated at different meridian settings, spaced over the surface of the cornea, by rotating the inner ring to a new position after each incision is completed. Throughout the surgical procedure, and thereafter if desired, the plurality of sensor probes 32 spaced along the arch 35 continue to measure the surface contour of the cornea and, most importantly, changes therein as the surgery proceeds.

For a perforating keratoplasty procedure, in which the cornea is removed in a circular cut prior to replacement of a cornea from a donor's eye or with an artificial lens, the knife blade 112 may be rotated 90 degrees relative to the handle 110 so that its cutting edge 112a is oriented perpendicular to a meridian of the cornea. In this latter position, with the knife at a fixed longitudinal position within the guide 40, rotation of the inner ring over a full circle would cause the knife to make a uniform circular cut of the cornea. In modifying the instrument for this procedure the electrical contacts made between the leads 32a . . . n of the respective probe sensors 30 must allow for full circle rather than half circle rotation, unless the knife is also positioned (or two knives are used) on the other side of the arch 45. Also, the width of the knife blade must be no more than the width of the guideway 40 in order to allow the blade to be rotated into a normal position with respect thereto.

Figure 7:
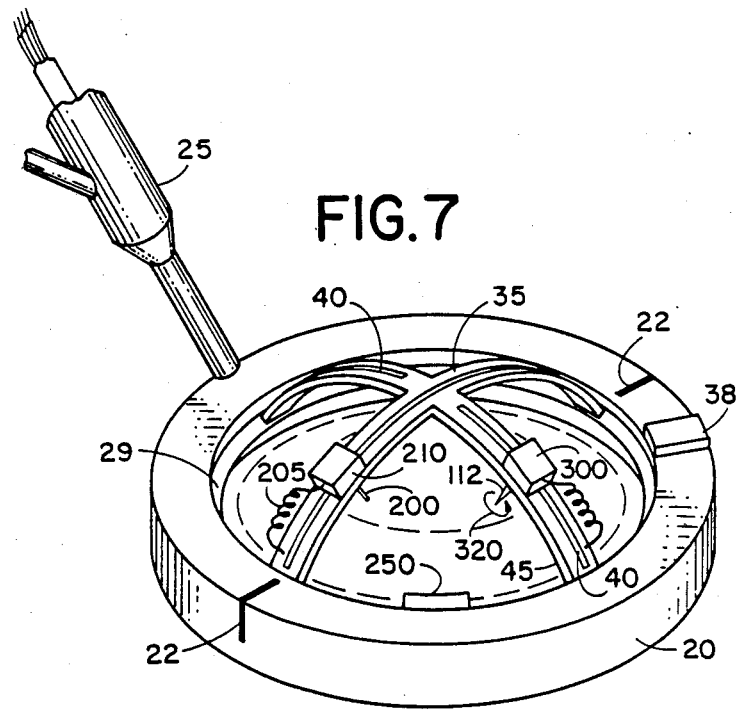
FIG. 7 is a pictorial view of a modified embodiment of the automated corneal surgery system of the present invention in which a single movable probe is used to map the corneal topography and the surgical knife is mounted for movement along a track for further automation of the surgical procedure.

A modified embodiment of the automated corneal surgery system of the present invention is illustrated in FIG. 7 which depicts a corneal topographic mapping instrument and surgical knife generally similar to that of the previously-described embodiment except in the following particulars. Instead of a plurality of spaced, fixed probe sensors a single probe sensor 230 is provided which is carried on a carriage 210 riding on a meridial track 220 formed on the arch element 35. (In this Figure similar elements are identified with the same reference numerals as the corresponding elements in the earlier-described embodiment.) The carriage is powered along the track by a small self-contained reversible motor (not shown) which by friction, or preferably cog-and-gear, engagement with the track produces linear translation of the carriage as the shaft of the motor is rotated. Drive signals for the carriage are supplied via coiled extendible lead 205 from the associated drive circuitry (not shown) under control of the micro-processor 50. By precisely monitoring the position of the probe sensor carriage 210 along the track the readings taken by the probe sensor 200 can be correlated to points on the corneal surface and a mapping obtained thereof as the inner ring element 29 is rotated to different meridial positions, in the same manner as accomplished with the earlier embodiment but utilizing just a single probe sensor instead of a plurality.

Another modification to the system is a similar movable carriage mounting of the surgical knife 300 on the guide which also serves as a track therefor. A coiled extendible cord 310 containing a plurality of leads provides electrical connections to the knife and associated carriage motor as it moves along the track. Control signals provided by the micro-processor (not shown) not only cause the associated motors to move the knife carriage 300 back and forth along the track and extend (and retract) the knife blade 112 as required, but also, as shown by the arrow 320, rotate the blade to the required orientation for either a radial keratotomy or perforating keratoplasty procedure as desired. In this latter procedure the knife blade 112 is positioned tangentially relative to the cornea at a location at or near the periphery thereof, and the knife depth is set for complete penetration (perforation) of the cornea. Rotation of the inner ring 29 through 180 degrees will then cause a semi-circular incision to be made in the cornea. Repositioning of the knife at the same relative location on the other side of the arch 45 then enables a matching semi-circular cut to be made to complete the circle. If desired the rotation of the inner ring 29 could be mechanized by the provision of a small stepping drive motor 250 mounted on either the inner ring or the outer fixed ring 20 with appropriate coupling provided by gears or the like for causing incremental movement of the inner ring relative to the fixed ring in response to control signals supplied by the micro-procesor.

Accordingly, this modified embodiment allows a fuller automation of the surgical operation as the microprocessor controls not only the depth positioning of the knife inside the cornea but also controls movement of the knife carriage 300 to translate the knife either radially to make the meridial incision in the radial keratotomy procedure or tangentially to make the circular incision in the perforating keratoplasty procedure. As before, the probe sensor 200 provides a mechanism for not only mapping the corneal surface configuration but also for monitoring intra-operationally the changes in the corneal surface contour caused by the surgical incisions. The inner ring 29 need only be rotated as required to position the arch element 35 over the desired corneal meridian to be measured and readings can be taken at a plurality of spaced points therealong by translation of the carriage 210. In fact, this monitoring of changes in the corneal contour can be carried out concurrently with the series of incisions made by the surgical knife as it is advanced to sucessive meridial positions spaced over the surface of the cornea.

The terms and expressions which have been employed in the foregoing specification are used therein as terms of description and not of limitation, and there is no intention, in the use of such terms and expressions, of excluding equivalents of the features shown and described or portions thereof, it being recognized that the scope of the invention is defined and limited only by the claims which follow.

What is claimed is:

1. An apparatus for mapping the contour of the corneal surface of the eye comprising:
    (a) sensor probe means adapted to be juxtaposed above the corneal surface for determining the positional location relative to a reference of a plurality of points distributed over the surface of the cornea, said sensor probe being mounted on support means attachable proximate the eye, said support means including movable means for moving said sensor probe in two dimensions to differing measuring locations over said corneal surface;
    (b) means for advancing said sensor probe means closer to said corneal surface;
    (c) means for monitoring the electrical resistivity between said sensor probe means and said corneal surface as said probe means is advanced towards same, thereby to determine the point of contact therewith; and
    (d) means for generating sets of data signals representative of both the respective positions of said points and the extent of advancement of said probe means at said point of contact.

2. An apparatus for mapping the contour of the corneal surface of the eye comprising:
    (a) sensor probe means, adapted to be juxtaposed above the corneal surface for determining the positional location relative to a reference of a plurality of points distributed over the surface of the cornea, said sensor probe means being mounted on a ring means attachable to the eye, said ring means including rotatable means for moving said sensor probe means to differing measuring locations above the corneal surface;
    (b) means for advancing said sensor probe means closer to said corneal surface;
    (c) means for monitoring the electrical resistivity between said sensor probe means and said corneal surface as said probe means is advanced towards same, thereby to determine the point of contact therewith; and
    (d) means for generating sets of data signals representative of both the respective positions of said points and the extent of advancement of said probe means at said point of contact.

3. The corneal contour mapping apparatus of claim 2 wherein said ring means has an outer ring and an inner ring, said inner ring including an arch element bridging portions thereof and having said probe sensor means mounted thereon, said arch element being rotatably movable relative to said outer ring.

4. The corneal contour mapping apparatus of claim 3, further characterized in that said probe sensor means has an associated motor means for incrementally advancing and retracting its probe tip.

5. The corneal contour mapping apparatus of claim 3 wherein said arch element bridges a diameter of said ring means, and rotation of said inner ring causes said probe sensor means mounted on said arch element to move along a circular path which is concentric with the center of said ring means.

6. The corneal contour mapping apparatus of claim 3, further including means for measuring the rotational displacement of said inner ring relative to said outer ring of said ring means.

7. The corneal contour mapping apparatus of claim 6, further including indicia means for rotationally aligning said inner ring to a predetermined reference orientation relative to said outer ring.

8. The corneal contour mapping apparatus of claim 6, wherein said rotational displacement measuring means generates data signals indicative of the rotational orientation of said inner ring relative to said outer ring.

9. The corneal contour mapping apparatus of claim 8, further including micro-processor means, coupled to receive said data signals from said rotational displacement measuring means and resistivity measurement signals and probe positional displacement signals from said probe sensor means, for generating a map representation of the contour of the corneal surface of the eye under measurement.

* * * * *